United States Patent [19]

Yoshida et al.

[11] 4,246,489
[45] Jan. 20, 1981

[54] LIQUID LEVEL DETECTOR FOR DETECTING A LIQUID LEVEL WHEN REACHING A PRESCRIBED HEIGHT

[75] Inventors: Mitsuo Yoshida, Yamato; Toshihiko Kihara, Yokohama; Hiroshi Nagasawa, Kawasaki, all of Japan

[73] Assignee: Tokyo Shibaura Electric Co., Ltd., Japan

[21] Appl. No.: 30,373

[22] Filed: Apr. 16, 1979

Related U.S. Application Data

[63] Continuation-in-part of Ser. No. 790,745, Apr. 25, 1977, abandoned.

[51] Int. Cl.³ ............................................. G01N 15/06
[52] U.S. Cl. ..................................... 250/577; 250/227
[58] Field of Search .............. 250/227, 577; 350/96.1; 73/293; 396/133, 135, 136, 137

[56] References Cited

U.S. PATENT DOCUMENTS

| | | |
|---|---|---|
| 3,120,125 | 2/1964 | Vasel ..................................... 250/577 |
| 3,384,885 | 5/1968 | Forbush ................................ 250/577 |
| 3,540,025 | 11/1970 | Levin et al. ........................... 356/136 |
| 3,553,666 | 1/1971 | Melone .................................. 250/577 |
| 3,639,770 | 2/1972 | Zizelmann ............................ 250/577 |
| 3,683,196 | 8/1972 | Obenhaus .............................. 250/577 |
| 3,977,790 | 8/1976 | Schweizer et al. ................... 356/136 |

*Primary Examiner*—David C. Nelms

*Attorney, Agent, or Firm*—Finnegan, Henderson, Farabow, Garrett & Dunner

[57] ABSTRACT

A liquid level detector for detecting whether a boundary surface between a liquid and a medium rises beyond a prescribed level comprises a rectangular prismatic refractor body formed of a material which only allows the transmission of a light having particular wavelengths and absorbs light having other wavelengths. The refractor body have first and second inclined flat surfaces and a base. The base of the refractor body is provided with a light-emitting element for projecting a beam of light having the particular wavelength and a photoelectric conversion element for converting the light to an electric signal. Each of these element is equidistantly spaced from the center of the base, and the optical axis of each of these elements defines an angle of 45° with each of the inclined surfaces of the refractor body. Where the first inclined surface contacts an medium, the light beam from the light-emitting element passes through the refractor body, is totally reflected from the first and second inclined surfaces, and finally enters the photoelectric conversion element. Where the first inclined surface contacts a liquid, the light beam from the light-emitting element passes through the refractor body, is refracted on the first inclined surface and enters the liquid, and the photoelectric conversion element receives substantially no light and generates no electric signal.

32 Claims, 9 Drawing Figures

LIQUID LEVEL DETECTOR FOR DETECTING A LIQUID LEVEL WHEN REACHING A PRESCRIBED HEIGHT

CROSS-REFERENCE TO THE RELATED APPLICATION

This is a continuation-in-part application of U.S. Patent Application Ser. No. 790,745 filed Apr. 25, 1977 now abandoned.

This invention relates to a liquid level detector for sensing a liquid level when it reaches a prescribed height.

A liquid level detector is generally utilized in various types of industries using a liquid and are provided in, for example, a chemical plant, a fuel tank of a vehicle, an automatic liquid-dispensing machine, etc. This liquid level detector detects the level of a liquid held in a liquid tank when it reaches a prescribed height, thereby indicating that said tank contains a required amount of liquid.

The prior art liquid level detector generally comprises a float lying on the surface of a liquid which moves up and down as the liquid level rises or falls, and a relay whose contact is rendered conducting or non-conducting interlockingly with the position of the float. Namely, the conventional liquid level detector converts the mechanical vertical movement of the float into the operative and inoperative conditions of the relay contact, and detects a liquid level reaching a prescribed height by an electric signal issued through the relay contact.

However, the customary liquid level detector has the drawback that the range of its application is limited by the undermentioned problems.

With the known liquid level detector, the relay contact which is mechanically operated is subject to wear during long use, possibly presenting an erroneous behavior and consequently resulting in a decline in reliability. An inflammable liquid, in particular, creates an explosive atmosphere when mixed with air. Therefore, sparks arising from the operation of a relay contact would perchance give rise to an explosion. For this reason, the prior art liquid level detector has failed to be used in detecting the level of an inflammable liquid.

It is accordingly an object of this invention to provide a liquid level detector adapated for application in various types of industries using a liquid.

Another object of the invention is to provide a liquid detector which remains highly reliable over a long, continuous use and can be operated with a high sensitivity.

Still another object of the invention is to provide a liquid level detector which does not give rise to accidents, for example, an explosion, even when an object of detection is an inflammable liquid.

According to an aspect of this invention, there is provided a liquid level detector for detecting whether a boundary surface between a liquid and a medium rises beyond a prescribed level, which comprises;
a refractor body formed of a material which only allows the transmission of a light having particular wavelengths and absorbs light having other wavelengths, said refractor body having at least one flat surface for contacting one of the liquid and medium, a light-emitting element for projecting a beam of light having the particular wavelengths transmittable through the refractor body to the flat surface thereof at a predetermined angle of incidence larger than the critical angle of the refractor body to the medium, and a photoelectric conversion element for converting the light totally reflected from the flat surface of the refractor body to an electric signal while the flat surface is in contact with the medium.

This invention can be more fully understood from the following detailed description when taken in conjunction with the accompanying drawings, in which.

Figure 1:
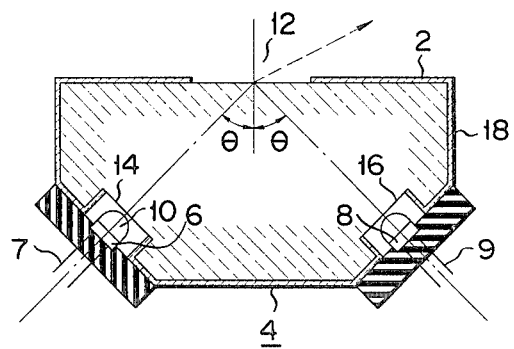
FIG. 1 is a cross sectional view of a fundamental arrangement of a liquid level detector according to one embodiment of this invention.

A liquid level detector whose fundamental arrangement is shown in FIG. 1 is positioned, as apparent from the following description, in contact with two media having different refractive indices. Where one of the two media is a liquid, a boundary therebetween is defined as a liquid level. Where both media are liquids, for example, where one of the media is water and the other is oil, then the boundary therebetween is similarly defined as a liquid level. The liquid level detector comprises a refractor 4 having a flat surface made to contact the surface of a liquid whose level has reached a prescribed height. This refractor body 4 is formed of transparent or colored glass or epoxy resin, and is required to have a fully larger refractive index (generally above 1.4 to 2.2) than a particular medium contacting said refractor body 4, for example, air or any other gas or a liquid, for example water, having a relatively small refractive index. Though admissibly formed into any shape, the refractor body 4 should have at least one flat surface made to contact the surface of a liquid whose level has reached a prescribed height.

The liquid level detector further comprises a light-emitting element 6 and photoelectric conversion element 8 provided to the refractor body 4. The light-emitting element 6 is an infrared light-emitting diode prepared from, for example, gallium arsenid (GaAs). The photoelectric conversion element 8 is a silicon photodiode, photo-transistor or photo-integrated circuit. Referential numerals 7, 9 denote the leads of the light-emitting element 6 and photoelectric conversion element 8 respectively. The light-emitting element 6 is so positioned as to project a light on the flat surface 2 through the refractor body 4. Where the flat surface 2 of the refractor body 4 contacts a gas, for example, air, then the light-emitting element 6 should be so disposed as to cause light entering the flat surface 2 of the refractor body 4 to be totally reflected. Where the liquid level detector is used to detect a boundary or liquid level between two kinds of liquid, then the light-emitting element 6 is so positioned as to cause light striking the flat surface 2 of the refractor body 4 to be totally reflected when said flat surface 2 contacts that of the two kinds of liquid which has a smaller refractive index. With the embodiment of FIG. 1, where the direction in which a maximum amount of light is projected from the light-emitting element 6 coincides with the light axis thereof, then an angle $\theta$ defined by said light axis with a normal intersecting the flat surface 2 of the refractor body 4 is chosen to be fully larger (for example 45°) than the critical angle $\alpha$ of the refractor body 4 relative to a particular medium. This critical angle $\alpha$ is expressed as follows from the known Snell's law:

$$\alpha = \operatorname{Sin}^{-1}(n_1/n_2)\ (n_2 \operatorname{Sin} \alpha = n_1 \operatorname{Sin}(\pi/2))$$

where:

$n_1$ = refractive index of a medium contacting the flat surface 2, namely, a gas or a liquid having a relatively small refractive index (with the refractive index of air taken to be 1)

$n_2$ = refractive index of the refractor body 4

The photoelectric conversion element 8 is also so set as to receive a light totally reflected from the flat surface 2. Namely, with the embodiment of FIG. 1, the light axis of the photoelectric conversion element 8 defines an angle $\theta$ with a normal perpendicularly crossing the intersection of the light axis of the light-emitting element 6 and the flat surface 2.

The light-emitting element 6 is preferred to send forth a focused light. To this end, the light-emitting portion of the light-emitting element 6 may be provided with a convex lens element 10 which focus a light emitted from the light-emitting element. Further, regions of the refractor body 4 other than the light paths should preferably be shut off from light. Namely, it is desired that not only the regions of the surface of the refractor body 4 other than a prescribed region 12 of the flat surface 2 lying around the intersection of the axis of the light-emitting element 6 and the flat surface 2, but also the inclined planes 14, 16 facing the light-emitting element 6 and photoelectric conversion element 8 be coated with light-shutting or light-impervious means 18, for example, a black layer to shut off a light entering the refractor body 4 from the outside.

The above-mentioned liquid level detector is fitted to the inner wall of a tank holding a liquid whose level is to be detected, with the flat surface 2 of the retractor body 4 of said detector made to face that height of the inner wall of said tank at which the liquid lies when filled in a prescribed quantity. For example, where the liquid is increasingly filled in the tank up to a prescribed quantity, then the liquid level detector detects this event through the undermentioned operation. Initially when a considerably small amount of liquid is held in the tank, the flat surface 2 of the refractor body 4 contacts a medium, for example, air contained in the tank. Accordingly, a light sent forth from the light-emitting element 6 is totally reflected from the flat surface 2 to the photoelectric conversion element 8. Where, however, the liquid is increased to a prescribed quantity with the level of the liquid raised until the liquid contacts the flat surface 2, then a light delivered from the light-emitting element 6 is only minimumly reflected from the flat surface 2, and is substantially refracted into the liquid. Therefore, a light issued from the light-emitting element 6 substantially ceases to enter the photoelectric conversion element 8. As apparent from the foregoing description, the level of a liquid when reaching a prescribed quantity can be detected according to whether the photoelectric conversion element 8 receives or does not receive a light from the light-emitting element 6.

Figure 2:
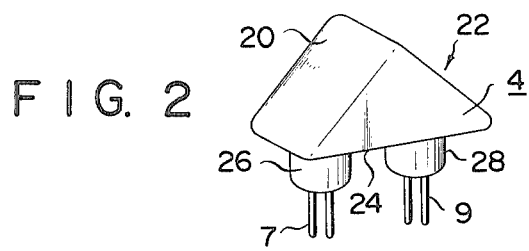
FIG. 2 is an oblique view of the liquid level detector of FIG. 1.
Figure 3:
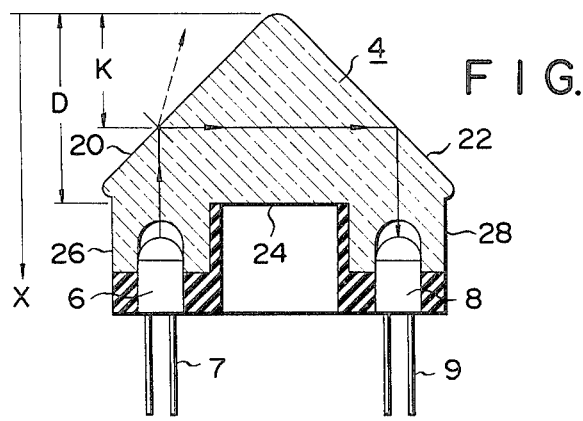
FIG. 3 is a longitudinal sectional view of the liquid level detector of FIG. 2.

There will now be described by reference to FIGS. 2 and 3 a liquid level detector according to another embodiment of this invention. The liquid level detector of FIGS. 2 and 3 has substantially the same construction as that of FIG. 1, the only difference lying in the shape of the refractor body 4. The refractor body 4 of the liquid level detector of FIGS. 2 and 3 is constructed in the rectangular prismatic form having first and second equally inclined surfaces 20, 22. Two parallel hollow projections 26, 28 receiving the light-emitting element 6 and photoelectric conversion element 8 respectively are erected on the base 24 of the refractor body 4 at right angles. Therefore, the light axes of the light-emitting element 6 and photoelectric conversion element 8 defined an angle of substantially 45° with a normal intersecting the inclined surfaces 20, 22 respectively. The light axes of both elements 6, 8 are equidistantly spaced from a perpendicular extending from the apex of the rectangular prismatic refractor body 4 to the base 24.

The liquid level detector of FIGS. 2 and 3 is fitted to the inner wall of a liquid tank such that at least the first inclined surface 20 receiving a light issued from the light-emitting element 6 is made to face the inner wall of the liquid tank. Where the first inclined plane 20 of the refractor body 4 contacts, for example, a gaseous medium contained in the liquid tank, then a light sent forth from the light-emitting element 6 passes through the refractor body 4, as shown in solid lines in FIG. 3, and is totally reflected from the first and second inclined surface 20, 22 to the photoelectric conversion element 8. Where the first inclined surface 20 of the refractor body 4 contacts a medium of liquid contained in the liquid tank, then a light issued from the light-emitting element 6 travels through the refractor body 4, as shown in a broken line in FIG. 3, and is refracted on the first inclined surface 20 into the liquid received to the tank. Accordingly, the photoelectric conversion element 8 substantially ceases to receive a light from the light-emitting element 6. Therefore, it is possible to judge whether a liquid is filled in the tank up to that height at which the liquid level detector is positioned by detecting whether or not the photoelectric conversion element 8 is rendered operative upon receipt of a light from the light-emitting element 6. Namely, detection of the absence of an output signal from the photoelectric conversion element 8 indicates that the level of a liquid filled in the tank has reached a prescribed height.

The liquid level detector of FIGS. 2 and 3 can more effectively reduce the effect of a light directly carried from the light-emitting element 6 into the photoelectric conversion element 8 than the liquid level detector of FIG. 1 and in consequence can be operated with higher sensitivity. With the liquid level detector of FIG. 1, the light-emitting element 6 faces the photoelectric conversion element 8 at a certain angle as seen from FIG. 1. Even where, therefore, the flat surface 2 of the refractor body 4 contacts a prescribed liquid, some amount of a light sent forth from the light-emitting element 6 is directly brought into the photoelectric conversion element 8. Namely, the photoelectric conversion element 8 receives not only a reflected light issued from the light-emitting element 6 as an electric signal but also a light acting as a noise. Unlike the liquid level detector of FIG. 1, the light emitting element 6 and photoelectric conversion element 8 of the liquid level detector of FIGS. 2 and 3 do not face each other, thereby substantially preventing a light from being transmitted directly from the light-emitting element 6 to the photoelectric conversion element 8 and in consequence enabling the liquid level detector of FIGS. 2 and 3 to present a more sensitive responsiveness.

Figure 4:
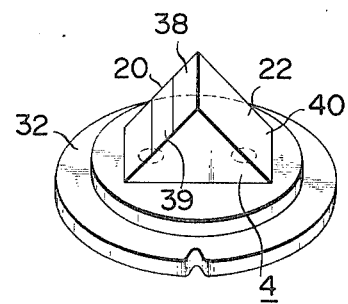
FIG. 4 is an oblique view of a liquid level detector according to another embodiment of the invention.
Figure 5:
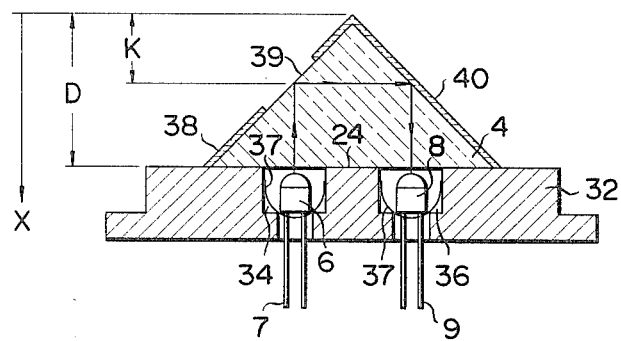
FIG. 5 is a longitudinal sectional view of the liquid level detector of FIG. 4.

There will now be described by reference to FIGS. 4 to 6 a liquid level detector according to still another embodiment of this invention. The refractor body 4 of the liquid level detector of FIGS. 4 to 5 has a rectangular prismatic form like that of FIGS. 2 and 3. The base 24 of the refractor body 4 is mounted on a substantially flat pedestal 32 made of light-impervious material, for example, metal. The pedestal 32 is bored with holes 34, 36 which receive the light-emitting element 6 and photoelectric conversion element 8 respectively. The refractor body 4 is secured to the pedestal 32 by means of thermal fusion, adhesive or screws.

In the hole 34 there may be provided with a concave mirror 37 which surrounds the light-emitting element 6 to reflect the light directed backward from the light-emitting element and to focus it. The light-emitting element 6 may be provided with the convex lens element 10 which focuses the light emitted from the light emitting element 6. The concave mirror 37 and convex lens element 10 cooperate to condense the light emitted from the light emitting element into a light beam to direct the same toward the surface 20. Light emitted from the light-emitting element 6 is usually divergent in nature. Where a divergent light is directed toward the flat surface 20, light rays are incident at various incidence angles onto the flat surfaces 20. In consequence, light beams totally reflected onto the flat surface 20 are decreased. Where, on the other hand, a flux of light focused or condensed by the mirror 37 or lens element 10 is incident onto the flat surface, light beams are incident at relatively equal incidence angles onto the flat surface. If the angle of incidence is equal to the critical angle α, focused incident light beams are totally reflected. In other words, a quantity of light incident onto the photoelectric conversion element 8 with the flat surface 20 not in contact with the liquid increasingly differs from a quantity of light incident onto the photoelectric conversion element 8 with the flat surface 20 in contact with the liquid is increased. As a result, the detection accuracy of a liquid level detector is increased.

The flat surface 20 is preferably covered with a liquid impervious layer 38 except for a predetermined region. The predetermined region is an area the center of which is a point when the flat surface 20 intersects with the optical axis of the light emitting element 6. That is, the region is an area on which a light beam emitted from the light emitting element is most intense. If a liquid level detector has a concave mirror 37 and convex lens element 10, that area onto which a light beam is incident corresponds to the above-mentioned predetermined region. The second inclined surface 22 may be covered with a reflection membrane 40. The second inclined surface 22 well serves the purpose only if it can direct a light reflected from the first inclined surface 20 toward the photoelectric conversion element.

If the liquid level detector is equipped with the light impervious layer 38 and the reflection membrane 40, only a light beam from the light emitting element 6 is incident onto the photoelectric conversion element 8 and thus there is hardly any light (regarded as a noise) incident from the outside onto the refractor body 4 through the liquid or medium and there is no risk that the detector will be erroneously operated by an external light.

The refractor body 4 used in the above-mentioned three embodiments shown in FIGS. 1 to 5 may be formed of a filter corresponding to the wavelength of a light issued from the light-emitting element 6. The light-emitting element is formed of, for example, gallium arsenide (GaAs). The gallium arsenide light-emitting element 6 emits, as already known in the art, a light having a wavelength of 9300 to 9500 Å (substantially 9400 Å). As a material for a refractor body 4 having a filtering function use might be made of, for example, a material which cuts off a light having a wavelength of at least 6000 Å. If the refractor body is formed of glass, it may be made of, for example, a Tellurium dioxide ($TeO_2$) or Vanadium dioxide ($V_2O_3$) series glass. If the refractor body is made of a resin, the following materials may be added to the resin:

(1) Kayaset Black A-N (trade name) manufactured by NIPPON KAYAKU CO., LTD.
(2) Kayalite Black BN (trade name) manufactured by NIPPON KAYAKU CO., LTD.
(3) Epoxy Black 9203 (trade name) Toyo Ink Mfg. Co., Ltd.
(4) HC Black 1-s (trade name) Hodogaya Chemical Co., Ltd.

Figure 6:
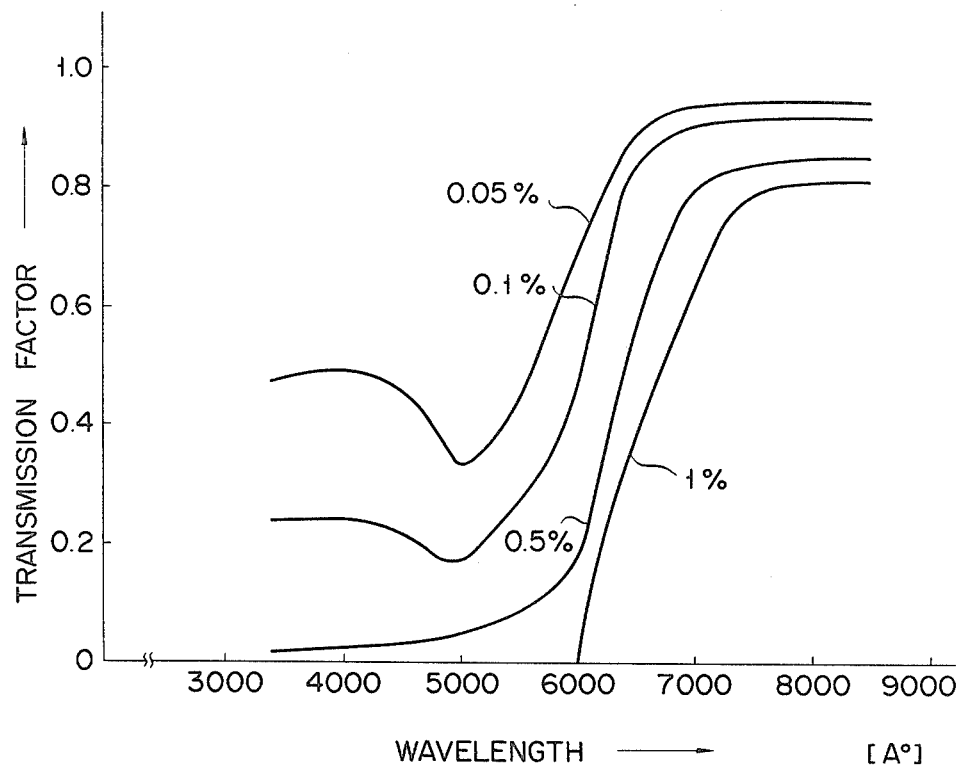
FIG. 6 is a graph showing the transmission factor of HC black 1-S.

Graph given in FIG. 6 shows the transmission factor of HC Black 1-S. In the graph, various values (0.05%, 0.1%, 0.5% and 1%) on the respective curves show the dye concentration of HC Black 1-S which was added to the resin. A light having a wavelength of 4000 to 8000 Å was incident upon a resin plate having a uniform thickness of about 1 mm. The respective values on the graph were derived from the light beams transmitted through the resin plate. It will be understood from the graph that, when the plate thickness is about 1 mm, a light having a wavelength of below 6000 Å is cut off.

Figure 7:
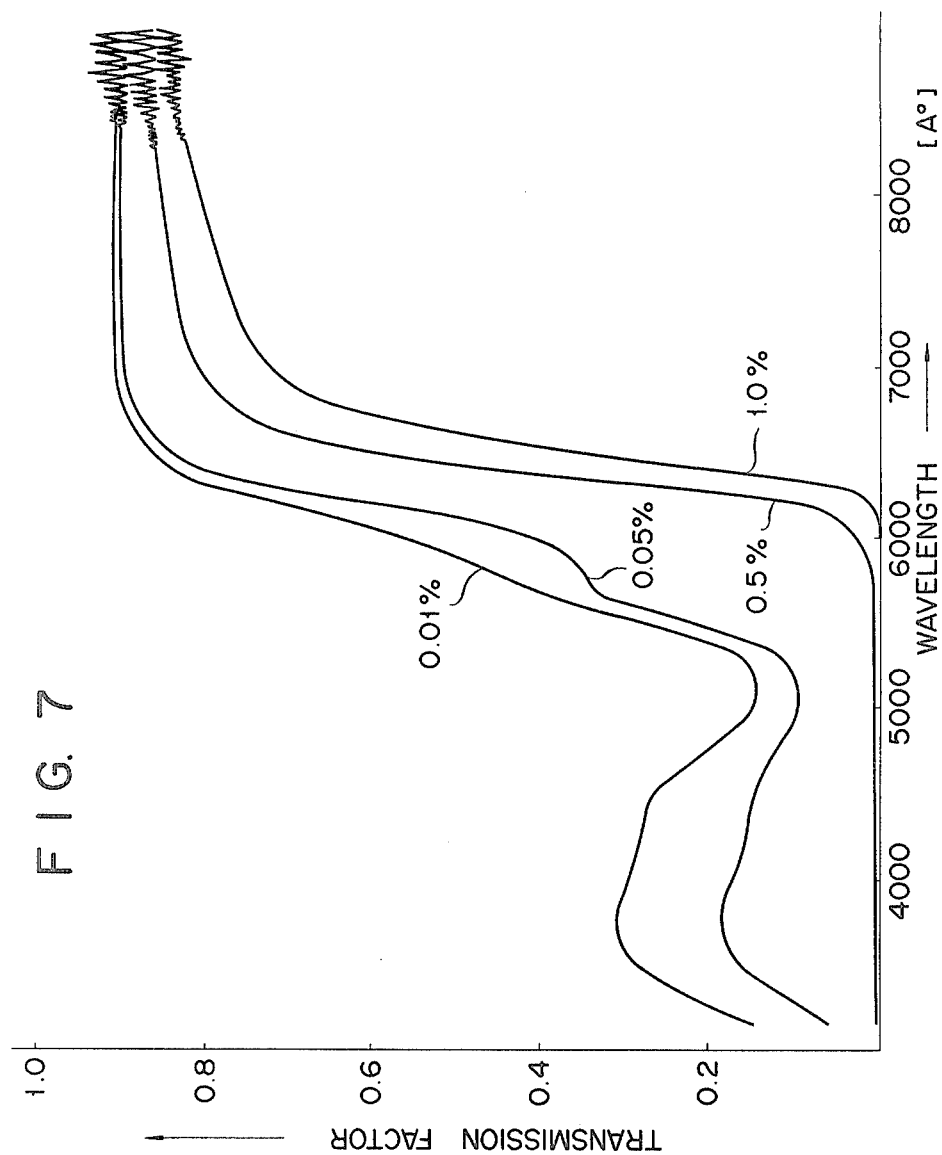
FIG. 7 is a graph showing the transmission factor of Kayalite Black BN.

Graph given in FIG. 7 shows the transmission factor of Kayalite Black BN. The values (0.01%, 0.05%, 0.5% and 1.0%) on the respective curves show the dye concentration of Kayalite Black BN which was added to the resin. A light having a wavelength of 4000 to 8000 Å was incident upon a resin plate having a substantially uniform thickness and the above-mentioned values were obtained from the light transmitted through the resin plate. From the graph it will be apparent that if the plate thickness is about 1 mm a light having a wavelength of below 6000 Å is cut off.

Now suppose that the refractor body 4 is made of a resin including the above-mentioned dye. If a light having a wavelength of below 6000 Å is incident from the outside to the photoelectric conversion element 8 through the refractor body 4, such light is cut off and not detected as a noise. As a result, the detection accuracy of the liquid level detector can be enhanced.

Table shows comparison data between a 1 mm-thick resin plate I which contains about 0.2% of Kayalite Black BN and 1 mm-thick resin plate II which contains no dyestuff.

TABLE

| LIGHT CURRENT RATIO | | LIGHT SOURCE | FLUORESCENT LIGHT | W LAMP | SUNLIGHT |
|---|---|---|---|---|---|
| RESIN | | I | 1 | 0.8 | 1 |
| | | II | 20 | 1 | 10 |

The data shows a current ratio between I and II.

Figure 8:
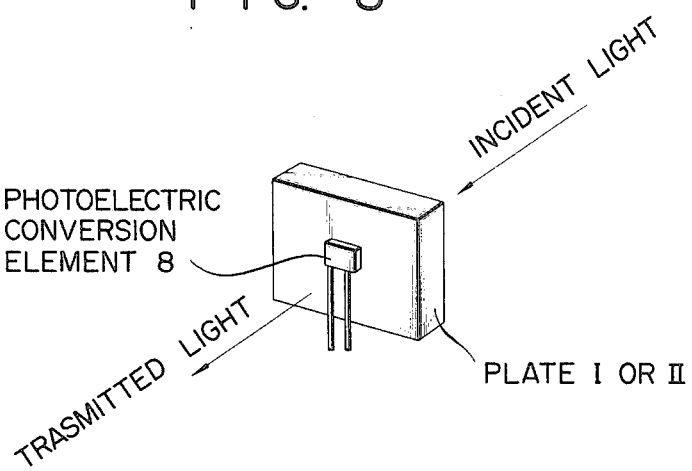
FIG. 8 is a testing arrangement for obtaining a comparison data between a resin plate I and a resin plate II.

In this case, the photoelectric conversion element 8 was disposed behind the plates I and II in FIG. 8 and light was incident from the front of the plate and the corresponding current values were obtained by the element 8. As will be evident from the Table, a light from the fluorescent lamp, a light from the tungsten lamp and a sunlight are used as a light source. As will be understood from the Table, light from the fluorescent lamp and sunlight are less transmissive to the plate I than to the plate II. This means that such light can hardly transmitted through the refractor body 4 to which is added a dyestuff. As already mentioned, only right beams from the light-emitting element 6 which are treated as a signal are transmitted through the refractor body 4, thus enhancing the detection accuracy of the detector. The refractor body 4 containing Kayalite Black BN shows no appreciable effect on a light from the tungsten lamp. In such a case, a light impervious layer 18, 38, 40 is provided on the refractor body, thereby decreasing an amount of light beams incident onto the refractor body from the outside. In this way, the detection accuracy of the detector can be enhanced.

Figure 9:
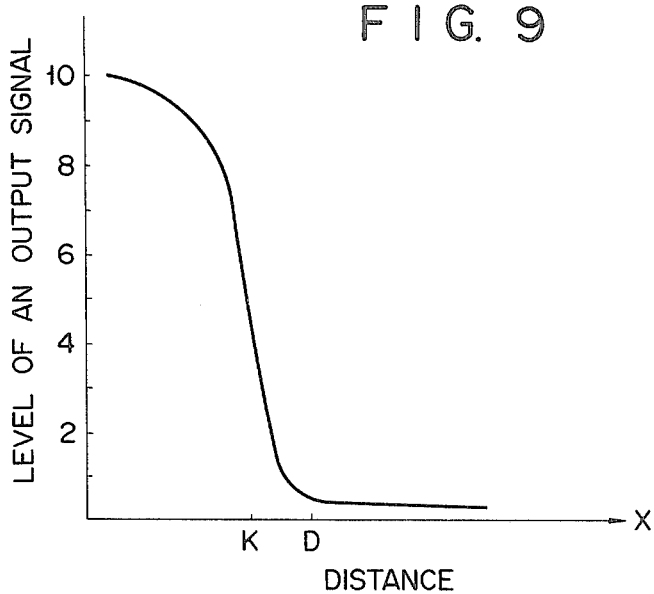
FIG. 9 is a coordinate system showing the characteristics of the liquid level detector of FIGS. 2 and 3.

FIG. 9 shows for referential purpose the characteristics of the liquid level detector of FIGS. 2 and 3 in the from of a coordinate system. The ordinate denotes the voltage level of an output signal from the photoelectric conversion element 8, and the abscissa represents a distance X extending, as shown in FIG. 3, from the apex of the prismatic refractor body 4 toward the base 24 thereof. The character K indicates a distance perpendicularly measured from the apex of the prismatic refractor body 4 up to the intersection of the light axis of the light-emitting element 6 and the first inclined plane 20. The character D shows a distance measured from the apex of the refractor body 4 up to the base 24 thereof. The curves of FIG. 6 denote changes in the voltage level of an output signal from the photoelectric conversion element 8, where the liquid level rises from the apex of the prismatic refractor body 4 to the base 24 thereof. Where the liquid level reaches a point spaced from the apex of the refractor body 4 by the distance K, then the voltage level of an output signal from the photoelectric conversion element 8 extremely drops, as seen from FIG. 6. Therefore, the liquid level detector according to the embodiment of FIGS. 4 and 5 can very sensitively detect the liquid level when it reaches a prescribed height.

The liquid level detector of this invention can be suitably used in various applications, such as in a gasoline tank of an automobile, automatic liquid dispenser, washing machine, a chemical plant using an inflammable liquid and a buzzer device of a bath.

What we claim is:

1. A liquid level detector for detecting whether a boundary surface between a liquid and a medium rises beyond a prescribed level, comprising:
   a refractor body having a refractor index larger than the refractive index of the medium and formed of a material which only allows the transmission of light having wavelengths within a selected wavelength band and absorbs light having wavelengths not within the selected wavelength band, said refractor body having at least one flat surface for contacting one of the liquid and medium;
   a light-emitting element for projecting a beam of light having the wavelengths within the selected wavelength band transmittable through the refractor body to the flat surface thereof at a pre-determined angle of incidence larger than the critical angle of the refractor body to the medium; and
   a photoelectric conversion element for converting the light totally reflected from the flat surface of the refractor body to an electric signal while the flat surface is in contact with the medium.

2. The liquid level detector according to claim 1, wherein the refractor body has two surfaces inclined to the flat surface, the light-emitting element and the photoelectric conversion element being located adjacent the respective inclined surfaces of the refractor body, each of said elements defining a respective light axis having an angle of incidence with the flat surface of the refractor body larger than the critical angle of the refractor body to the medium.

3. The liquid level detector according to claim 1, wherein the refractor body is a rectangular prism having two inclined surfaces, and the light-emitting element and photoelectric conversion element are located adjacent the base of the rectangular prism, each of said elements defining a respective light axis which intersects said inclined surfaces at an angle of 45°.

4. The liquid level detector according to claim 3 further comprising a pedestal, the base of the rectangular prism being securely mounted to said pedestal, said pedestal having holes into which the light-emitting element and photoelectric conversion elements are respectively received.

5. The liquid level detector according to claim 1 further comprising a light-focusing lens for focusing the beam of light emitted by the light-emitting element.

6. The liquid level detector of claim 3 wherein one of said inclined surfaces is covered by a reflective membrane.

7. The liquid level detector of claim 1 wherein said light-emitting element is an infrared light-emitting diode.

8. The liquid level detector of claim 1 wherein said refractor body is formed from a tellarium dioxide series glass.

9. The liquid level detector of claim 1 wherein said refractor body is formed from a vanadium oxide series glass.

10. The liquid level detector of claim 1 wherein said refractor body is made of a resin including Kayaset Black A-N.

11. The liquid level detector of claim 1 wherein said refractor body is made of a resin including Kayalite Black BN.

12. The liquid level detector of claim 1 wherein said refractor body is made of a resin including Epoxy Black 9203.

13. The liquid level detector of claim 1 wherein said refractor body is made of a resin including HC Black 1-s.

14. A liquid level detector for detecting whether a boundary surface between a liquid and a medium rises beyond a prescribed level comprising:

a refractor body having a refractive index larger than the refractive index of the medium and formed of a material which only allows the transmission of light having wavelengths within a selected band and absorbs light having wavelengths not within the selected band, said refractor body having at least one flat surface for contacting one of the liquid and medium;

a light-emitting element for projecting a beam of light having the wavelengths within the selected band transmittable through the refractor body to the flat surface thereof at a predetermined angle of incidence larger than the critical angle of the refractor body to the medium; and a photoelectric conversion element for converting the light totally reflected from a part of the flat surface of the refractor body to an electrical signal while said flat surface part is in contact with the medium; and a light-impervious layer covering the refractor body but leaving said flat surface part exposed.

15. The liquid level detector according to claim 14, wherein the refractor body has two surfaces inclined to the flat surface, the light-emitting element and the photoelectric conversion element being located adjacent the respective inclined surfaces of the refractor body, each of said elements defining a light axis having an angle of incidence with the flat surface of the refractor body larger than the critical angle of the refractor body to the medium.

16. The liquid level detector according to claim 14, wherein the refractor body is a rectangular prism having two inclined surfaces, the light-emitting element and photoelectric conversion element are located adjacent the base of the rectangular prism, each of said elements defining a respective light axis which intersects said inclined surfaces at an angle of 45°.

17. The liquid level detector according to claim 14 further comprising a pedestal, the base of the rectangular prism being securely mounted to said pedestal, said pedestal having two holes into which the light-emitting element and photoelectric conversion element are respectively received.

18. The liquid level detector according to claim 14 further comprising a light focusing lens for focusing the beam of light emitted by the light-emitting element.

19. A liquid level detector for detecting whether a boundary surface between a liquid and a medium rises beyond a prescribed level, comprising:

a refractor body having a refractive index larger than the refractive index of the medium and formed of a material which only allows the transmission of infrared light and absorbs other light, said refractor body having at least one flat surface for contacting one of the liquid and medium;

an infrared light-emitting element for projecting a beam of infrared light transmittable through the refractor body to the flat surface thereof at a predetermined angle of incidence larger than the critical angle of the refractor body to the medium; and a photoelectric conversion element for converting the infrared light totally reflected from the flat surface of the refractor body to an electric signal while the flat surface is in contact with the medium.

20. The liquid level detector according to claim 19, wherein the refractor body has two surfaces inclined to the flat surface, the light-emitting element and photoelectric conversion element being located adjacent the respective inclined surfaces of the refractor body, each of said elements defining a respective light axis having an angle of incidence with the flat surface of the refractor body larger than the critical angle of the refractor body to the medium.

21. The liquid level detector according to claim 19, wherein the refractor body is a rectangular prism having two inclined surfaces, and the light-emitting element and photoelectric conversion element are located adjacent the base of the rectangular prism, each of said elements defining a respective light axis which intersects said inclined surfaces at an angle of 45°.

22. The liquid level detector according to claim 21 further comprising a pedestal, the base of the rectangular prism being securely mounted to said pedestal, said pedestal having holes into which the light-emitting element and photoelectric conversion elements are respectively received.

23. The liquid level detector according to claim 19 further comprising a light-focusing lens for focusing the beam of light emitted by the light-emitting element.

24. The liquid level detector of claim 19 wherein said light-emitting element is prepared from gallium arsenid and said refractor body is formed from an epoxy resin.

25. The liquid level detector of claim 21 wherein one of said inclined surfaces is covered by a reflective membrane.

26. The liquid level detector of claim 19 wherein said light-emitting element is an infrared light-emitting diode.

27. The liquid level detector of claim 19 wherein said refractor body is formed from a tellarium dioxide series glass.

28. The liquid level detector of claim 19 wherein said refractor body is formed from a vanadium oxide series glass.

29. The liquid level detector of claim 19 wherein said refractor body is made of a resin including Kayaset Black A-N.

30. The liquid level detector of claim 19 wherein said refractor body is made of a resin including Kayalite Black BN.

31. The liquid level detector of claim 19 wherein said refractor body is made of a resin including Epoxy Black 9203.

32. The liquid level detector of claim 19 wherein said refractor body is made of a resin including HC Black 1-s.

* * * * *